(12) United States Patent
Payeli et al.

(10) Patent No.: US 12,310,624 B2
(45) Date of Patent: May 27, 2025

(54) FOLLICULAR FLUID ASPIRATION

(71) Applicant: SHIVANI SCIENTIFIC INDUSTRIES PVT LTD, Maharashtra (IN)

(72) Inventors: Sravan Kumar Payeli, Bangalore (IN); Pavani Srividya Mocharla, Bangalore, IN (US)

(73) Assignee: SHIVANI SCIENTIFIC INDUSTRIES PVT LTD, Thane (IN)

( * ) Notice: Subject to any disclaimer, the term of this patent is extended or adjusted under 35 U.S.C. 154(b) by 997 days.

(21) Appl. No.: 17/297,384

(22) PCT Filed: Jul. 2, 2019

(86) PCT No.: PCT/IN2019/050491
§ 371 (c)(1),
(2) Date: May 26, 2021

(87) PCT Pub. No.: WO2020/110137
PCT Pub. Date: Jun. 4, 2020

(65) Prior Publication Data
US 2022/0031360 A1 Feb. 3, 2022

(30) Foreign Application Priority Data
Nov. 27, 2018 (IN) .............................. 201841044740

(51) Int. Cl.
*A61B 17/43* (2006.01)
*A61B 17/34* (2006.01)
(52) U.S. Cl.
CPC .......... *A61B 17/43* (2013.01); *A61B 17/3403* (2013.01); *A61B 2017/3413* (2013.01)
(58) Field of Classification Search
CPC ...... A61B 17/425; A61B 17/43; A61B 17/435
(Continued)

(56) References Cited

U.S. PATENT DOCUMENTS

| 4,824,434 A | 4/1989 | Seitz, Jr. |
| 6,461,302 B1 | 10/2002 | Thompson |

(Continued)

FOREIGN PATENT DOCUMENTS

| CN | 101692982 A | 4/2010 |
| CN | 204133576 U | 2/2015 |

(Continued)

OTHER PUBLICATIONS

International Search Report and Written Opinion, mailed Dec. 3, 2019, for International Application No. PCT/IN2019/050491, 7 pages.

(Continued)

*Primary Examiner* — Samuel G Gilbert (57) ABSTRACT

The present subject matter discloses a device and system of aspirating follicular fluid. In an example, an ovum pick up (OPU) device for aspirating follicular fluid includes a needle having a first end and a second end, opposite to the first end. The first end of the needle is to pierce through an ovarian follicle to aspirate the follicular fluid from the ovarian follicle by a suction force. The OPU device includes a connector having a channel to receive the second end of the needle. The OPU device further includes an elastic tube connected to the connector. The second end of the needle passes through the channel and inside the elastic tube. The elastic tube is compressible, while locating the ovarian follicle and piercing the needle through the ovarian follicle, to regulate the suction force during aspiration of the follicular fluid between two follicles.

20 Claims, 9 Drawing Sheets

(58) Field of Classification Search
USPC .............................................. 604/19, 35, 532
See application file for complete search history.

(56) References Cited

U.S. PATENT DOCUMENTS

| | | | |
|---|---|---|---|
| 6,464,302 B1 | 10/2002 | Huang | |
| 2005/0143619 A1 | 6/2005 | Spittle et al. | |
| 2006/0205073 A1 | 9/2006 | Oktay et al. | |
| 2012/0029354 A1* | 2/2012 | Mark ................ | A61B 10/0275 |
| | | | 606/41 |
| 2015/0343121 A1* | 12/2015 | Kobida ............... | A61M 1/7411 |
| | | | 604/187 |
| 2016/0113680 A1 | 4/2016 | Hodgson et al. | |
| 2018/0214179 A1 | 8/2018 | Inoue et al. | |

FOREIGN PATENT DOCUMENTS

| | | |
|---|---|---|
| CN | 204814119 U | 12/2015 |
| CN | 107949335 A | 4/2018 |
| CN | 108143471 A | 6/2018 |

OTHER PUBLICATIONS

International Preliminary Report on Patentability, dated May 25, 2021, for International Application No. PCT/IN2019/050491, 6 pages.

* cited by examiner

FOLLICULAR FLUID ASPIRATION

BACKGROUND

Assisted reproductive techniques (ART) facilitate in infertility treatment of couples who are unable to conceive by natural means. In ART, male and female gametes (ovum and sperm) are collected from the couples which are then used for fertilization. In vitro Fertilization (IVF) is a type of ART in which male and female gametes are collected from the body of the prospective parents and are mixed together to allow fertilization in vitro, i.e., outside the body, in a culture media within a controlled environment, such as a laboratory. The in vitro fertilization of ovum by the sperm cells results in development of embryos. The embryos are assessed and transferred to the uterus of the prospective mother for further development.

BRIEF DESCRIPTION OF DRAWINGS

The following detailed description references the drawings, wherein.

DETAILED DESCRIPTION

IVF techniques involve collection of male and female gametes from bodies of the prospective parents. The female gametes called ova (eggs) are collected from the follicles of ovary of the prospective mother. The ovaries are stimulated by injecting hormones which enable to form multiple follicles over the surface and inside the ovary. The follicles appear like fluid-filled spherical structurers. Each follicle may contain about 1.5 ml to about 2.5 ml of follicular fluid. An ovum is generally disposed in the follicular fluid. These follicles are randomly distributed inside or on the surface of the ovary. For IVF, the follicular fluid containing the ovum is to be collected from the follicles.

A conventional system for collection of follicular fluid includes an ultrasound probe which provides a visual image of the follicles. A needle is mounted on the ultrasound probe, where the needle pierces through the wall of the follicles to aspirate out the follicular fluid by suction force. The needle has a lumen through-out. The needle is mounted on the ultrasound probe through a needle guide. The needle guide is fixed to the ultrasound probe to facilitate front and back movements of the needle for puncturing the follicles. The needle guided by the ultrasound probe is passed through the ovary to reach the follicles. The ultrasound probe facilitates in locating the follicles in the ovary and the needle guide facilitates movement of the needle for piercing the follicles. The conventional system further includes a collection chamber, a suction pump, and connecting tubes.

The needle is connected to the collection chamber through a first connecting tube. The suction pump is connected to the collection chamber by a second connecting tube. The connecting tubes are made of plastic. For collection of the follicular fluid, the needle is inserted, by a physician, into a follicle of the ovary. The physician is guided based on the visuals generated by the ultrasound probe. As, the suction pump is turned on, the suction pump draws out air from the collection chamber through the second connecting tube. Thus, fluid pressure inside of the collection chamber reduces, which results in a suction force acting along the first connecting tube. This suction force is conveyed through the first connecting tube to the tip of the needle and is applied inside the follicle. Due to this suction force, the follicular fluid is aspirated in the first connecting tube and gets accumulated in the collection chamber.

Conventionally, during collection of the follicular fluid, after complete aspiration of a single follicle, the needle is passed through inter follicular tissue (tissues of the ovary) to reach another follicle. This inter follicular tissue consists of blood vessels. Thus, when the needle is passed from one follicle to another, the suction force acts on the punctured blood vessels of the ovary which lead to aspiration of blood. In addition, due to the positive blood pressure in the punctured blood vessels, blood is pumped into the needle. This aspirated blood from the ovary mixes with the follicular fluid accumulated in the collection chamber thereby causing contamination of the follicular fluid. Blood stains in the follicular fluid alters the normal physiological composition of the follicular fluid. An IVF performed with ovum collected from blood stained follicular fluid may result in sub optimal fertilization rates. Further, the ovary may be subjected to trauma and strain due to aspiration of blood from the ovary and due to the suction force, there may be internal bleeding in the ovary. Also, constant application of the suction force may aspirate small portions of stroma tissue of the ovary which may contaminate the follicular fluid and may causes loss of ovum.

The present disclosure describes approaches in which, a compressible elastic tube is used to regulate the suction force, while locating the ovarian follicle and piercing the needle through the ovarian follicle simultaneously, during aspiration of the follicular fluid. Since, the suction force is regulated, the aspiration of blood from the ovary may be reduced or eliminated. Thus, by using the system(s) or ovum pick up (OPU) device(s) of the present disclosure, presence of blood stains in the aspirated follicular fluid may be reduced or eliminated, thereby, increasing the fertilization rates and facilitating an improved IVF outcome and patient care by minimizing the unwanted excess suction force on the ovary.

The present disclosure describes example implementations of system(s) and OPU device(s) for aspirating follicular fluid from ovarian follicles and controlling the aspiration pressures. In an example, a system for aspirating follicular fluid is described. The system includes a collection chamber for accumulation of the follicular fluid, a suction pump coupled to the collection chamber. The suction pump is operable to generate a suction force to aspirate the follicular fluid from an ovarian follicle. The system includes a needle having a first end and a second end, opposite to the first end. The first end of the needle is to pierce through the ovarian follicle to aspirate the follicular fluid from the ovarian follicle by the suction force. The system includes a connector having a channel to receive the second end of the needle and an elastic tube connected to the channel. The second end of the needle passes through the channel and reaches inside the elastic tube. The elastic tube is compressible to regulate the suction force generated by the suction pump while locating the ovarian follicle and piercing the needle through the ovarian follicle, simultaneously, during the aspiration of follicular fluid.

Thus, with the system, as described above, the suction force may be generated and/or increased when the needle is inside the follicle and may be reduced and/or eliminated when the needle is passed through the tissues of the ovary between two follicles or when the needle is out of the follicle. In an example, the first elastic tube may be compressed to reduce the suction force and decompressed to increase the suction force generated by the suction pump. Thus, when the needle passes through the ovarian tissue between two follicles, the elastic tube may be pinched to compress which will reduce or eliminate the suction force thereby preventing uncontrolled aspiration of blood from the blood vessels or tissues of the ovary. When the needle enters inside the follicle, the elastic tube may be decompressed thereby applying the suction force inside the follicle to aspirate the follicular fluid through the needle into the collection chamber. Thus, with the system(s) and OPU device(s) of the present disclosure the suction force may be controlled in real-time while performing the process of collection of the follicular fluid.

The following detailed description refers to the accompanying drawings (drawn not to the scale). Wherever possible, the same reference numbers are used in the drawings and the following description to refer to the same or similar parts. While several examples are described in the description, modifications, adaptations, and other implementations are within the scope of controlling the suction pressure inside the follicle and ovary with a pinch system in real time. Accordingly, the following detailed description does not limit the disclosed examples. Instead, the proper scope of the disclosed examples may be defined by the appended claims.

Figure 1:
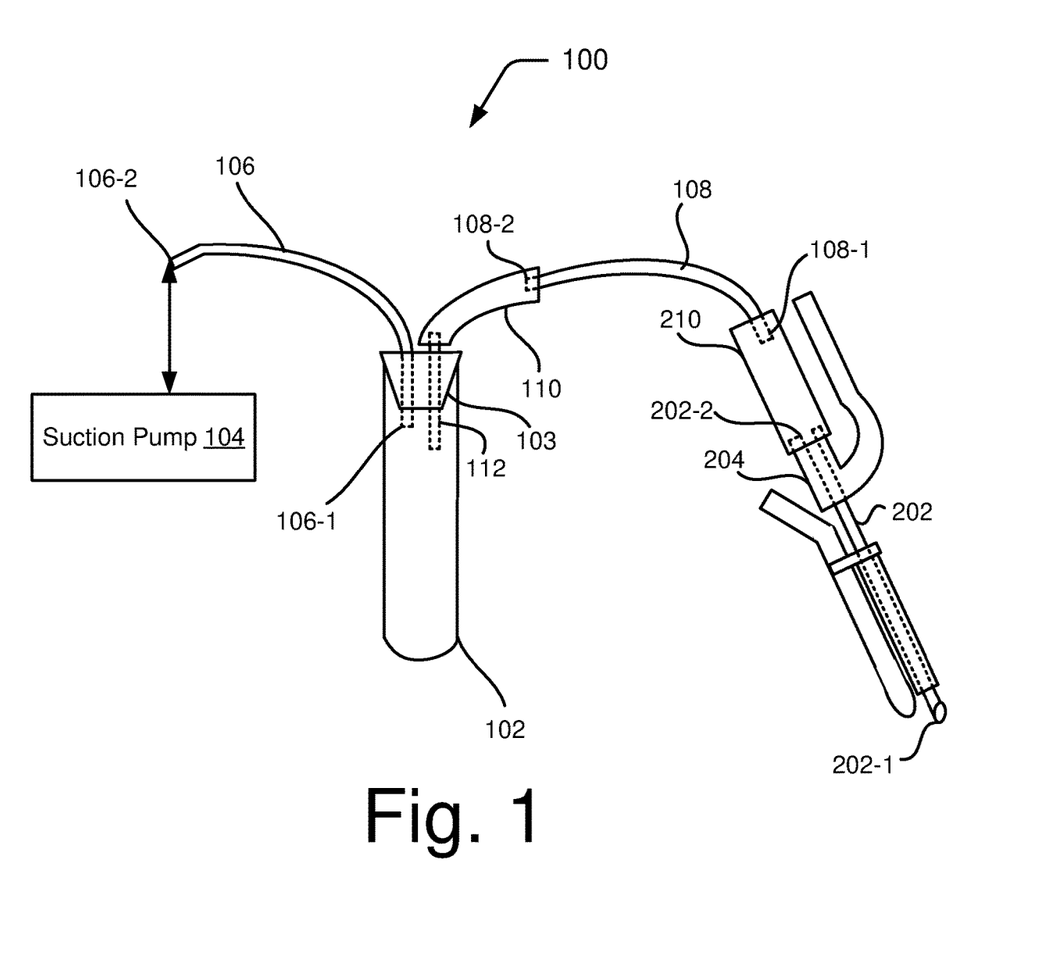
FIG. 1 illustrates a system for aspirating follicular fluid from ovarian follicles, according to an example.

FIG. 1 illustrates a system 100 for aspirating follicular fluid from ovarian follicles, according to an example. The system 100 may be operated by a physician for collection of follicular fluid from ovarian follicles. The system 100 includes a collection chamber 102. In an example, the collection chamber 102 may be a disposable container made of glass or plastic. In an example, the collection chamber may have a volume of 14 ml. The follicular fluid aspirated by the system 100 gets accumulated in the collection chamber 102. As shown in FIG. 1, the collection chamber 102 is closed by a stopper 103. The stopper 103 is air-tight. In an example, the stopper 103 is made of an elastic material such as rubber or silicon.

The system 100 includes a suction pump 104 coupled to the collection chamber 102. As shown in FIG. 1, the suction pump 104 is coupled to the collection chamber 102 through a connecting tube 106. The connecting tube 106 has a first end 106-1 which resides inside the collection chamber 102 and a second end 106-2 which is coupled to the suction pump 104 to aspirate air in the collection chamber and create vacuum inside the collection chamber 102. The second end 106-2 of the connecting tube may be coupled to the suction pump 104 through coupling elements (not shown). The first end 106-1 of the connecting tube 106 passes through the stopper 103 inside the collection chamber 102. The connecting tube 106 is also referred to as a first connecting tube 106. Although in FIG. 1, a single collection chamber 102 is shown, in other examples, there may be multiple collection chambers connected in tandem. In an example, a set of collection chambers may be connected between the suction pump 104 and the collection chamber 102, where collection chambers in the set are connected through a cascade connection of connector pipes. Such an example with multiple collection chambers is illustrated later in the description with reference to FIG. 8.

Figure 2:
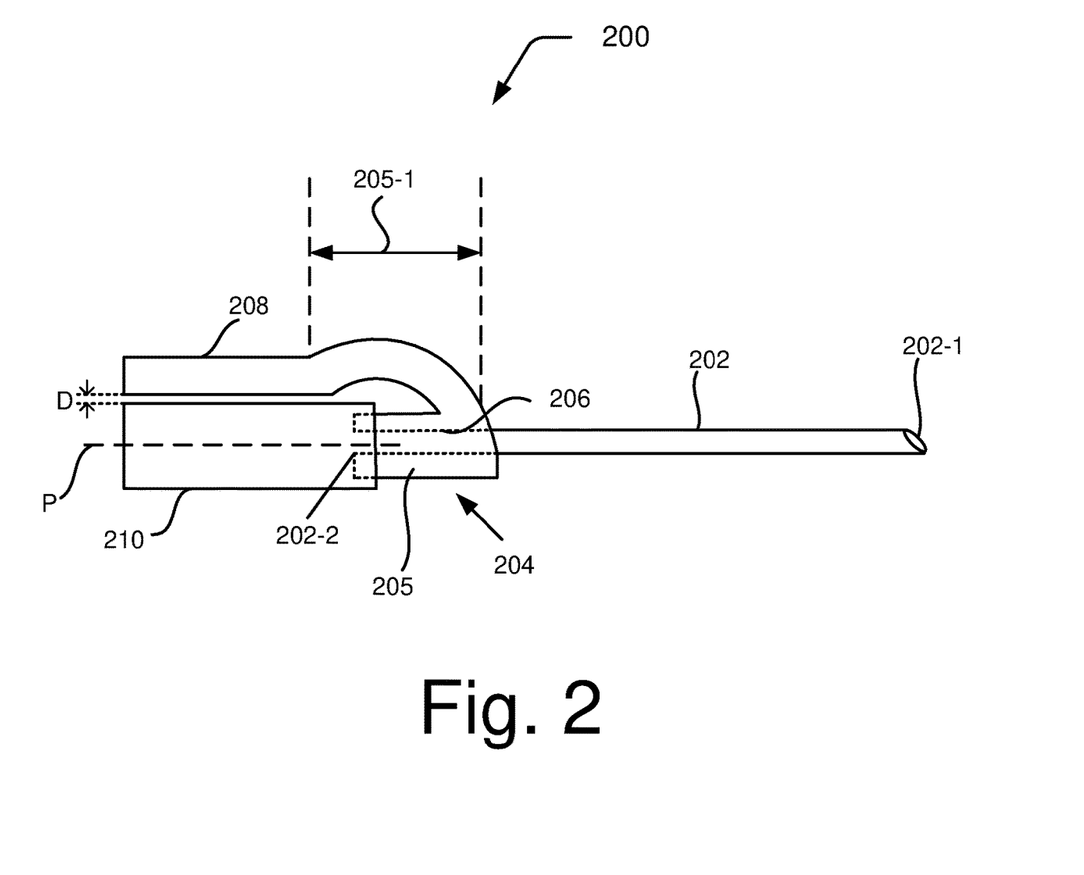
FIG. 2 illustrates an ovum pick up (OPU) device for aspirating follicular fluid from ovarian follicles, according to an example.

The system 100 includes an OPU device 200. The OPU device 200 is illustrated in detail with reference to FIG. 2. The OPU device 200 includes a needle 202. The needle 202, as shown in FIG. 2, is a single lumen needle having a first end 202-1 and a second end 202-2, opposite to the first end 202-1. Although in FIG. 2, a single lumen needle is shown, in an example, a needle with multiple lumens may also be used in the OPU device 200. The first end 202-1 of the needle 202 is guided with the help of a needle guide (not shown) fitted to an ultrasound probe by the physician and passed inside the body of the prospective mother. The first end 202-1 can pierce through an ovarian follicle to aspirate the follicular fluid from the ovarian follicle. In an example, the lumen of the needle 202 has a diameter ranging between about 0.6 mm to about 1.6 mm that allow ovum (oocyte cumulus complex) collection from the follicle.

The OPU device 200 includes a connector 204. The connector 204 includes a main body 205 with a channel 206 to receive the second end 202-2 of the needle 202. In an example, the main body 205 may be an elongated portion having a cylindrical structure. The channel 206 is a through-hole or a passage formed in the main body 205 through which the needle 202 can pass. In an example, the main body 205 resembles the structure of an annular cylinder. The connector 204 further includes a handle 208 protruding out from the main body 205 and extending longitudinally away from the first end 202-1 of the needle 202. The handle 208 is integral to the connector 204 and may be formed by plastic molding or may be a separate unit attached to the main body 205. In an example, the handle 208 has a length ranging between about 2 centimeter (cm) to about 7 cm. The handle 208 may have a triangular or circular cross-section. In an example, the handle 208 has a width ranging from about 0.5 cm to about 2 cm and has a height ranging from about 0.5 cm to about 3 cm. In an example, the connector 204 is typically formed from plastic or metal or combination thereof.

As shown in FIG. 2, the connector 204 includes a slope region 205-1. The handle 208 is connected to the main body 205 through the slope region 205-1. In an example, the slope region 205-1 is a semicircular slope with one end connected to the main body 205 and the other end connected to the handle 206. In an example, the slope region 205-1 may be formed by a beveled edge between the handle 208 and the main body 205 of the connector 204. Other features of the handle 208 are explained later in the description with reference to FIG. 5.

The OPU device 200 includes an elastic tube 210 connected to the channel 206. The elastic tube 210 may be a bulb shaped compressible structure, like a cylinder with a hollow channel, that can bear a pressure of 200 millimeter (mm) of mercury or above. In an example, the elastic tube 210 is formed from oocyte (egg) safe elastic materials, such as rubber or silicon or any other material. The elastic tube 210 may be snug fitted to an end of the connector 204. The handle 208 of the connector 204 extends along a length of the elastic tube 210 and overlays on the elastic tube 210. The handle 208 is parallel to a horizontal plane P passing through the elastic tube 210. The handle 208 is separated from the elastic tube by a distance 'D'. In an example, the distance 'D' ranges between about 0.5 millimeter (mm) to about 10 mm. In an example, the handle 208 is positioned with respect to the elastic tube 210, such that the elastic tube 210 is pinched by the movement of the index finger and the thumb towards each other, while the handle 208 is gripped between the index finger and the thumb ergonomically to facilitate the efficient pinch controlling the suction pressure. The slope region 205-1 of the connector 204 facilitates fitting of the elastic tube 210 to keep the handle 208 in proximity to the elastic tube 210, so that the elastic tube 210 and the handle 208 may be gripped and manipulated by the index finger and the thumb, simultaneously.

In an example, the elastic tube 210 has a length ranging from about 1 centimeter to about 10 centimeters or more and an inner diameter ranging from about 0.1 centimeter to about 1.5 centimeters or more. The end of the connector 204 to which the elastic tube 210 is fitted is opposite to the end of the connector 204 through which the needle 202 enters. The second end 202-2 of the needle 202 passes through the channel 206 and inside the elastic tube 210. The elastic tube 210 is also referred to as the first elastic tube 210. In an example, the elastic tube 210 has an inner diameter one of equal to and greater than an outer diameter of the needle 202.

The system 100 further as showed in the FIG. 1 includes a connecting tube 108 that connects the first elastic tube 210 with the collection chamber 102. The connecting tube 108 is also referred to as a second connecting tube 108. The second connecting tube 108 carries the follicular fluid aspirated out of the follicles from the first elastic tube 210 to the collection chamber 102. In an example, the second connecting tube 108 is formed from plastic. The second connecting tube 108 has a first end 108-1 that enters into the first elastic tube 210 and a second end 108-2 opposite to the first end 108-1.

When the suction pump 104 is turned on, the suction pump 104 can draw out air form the collection chamber 102 through the first connecting tube 106 thereby creating a negative fluid pressure in the collection chamber 102. Due to the negative fluid pressure in the collection chamber 102, a suction force is conveyed along the second connecting tube 108 to the first end 202-1 of the needle 202. The suction force at the first end 202-1 of the needle 202 draws out the follicular fluid from the follicles, which is then carried by the second connecting tube 108 to the collection chamber 102. The first elastic tube 210 is compressible to regulate the suction force, while locating the ovarian follicle and piercing the needle through the ovarian follicle, during aspiration of the follicular fluid.

The system 100 includes a second elastic tube 110 connected between the second connecting tube 108 and the collection chamber 102. The second end 108-2 of the second connecting tube 108 enters into the second elastic tube 110. The second elastic tube 110 is compressible to reduce or eliminate the backflow of aspirated follicular fluid from the needle 202 or second connecting tube 108 back to the follicle due to the negative pressure present in the ovary. The system 100 includes a third connecting tube 112 which enters into the second elastic tube 110 and carries the follicular fluid from the second elastic tube 110 to the collection chamber 102.

Figure 3:
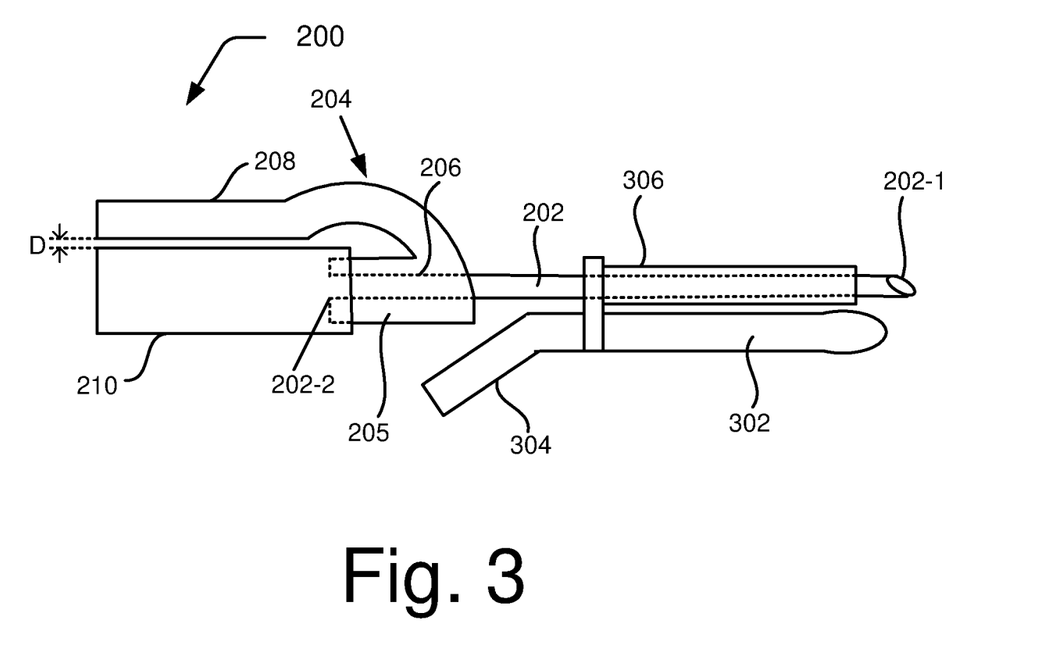
FIG. 3 illustrates a portion of the system for aspirating follicular fluid where a needle of the OPU device is mounted on an ultrasound probe, according to an example.

The system 100 further includes an ultrasound probe 302 on which the needle 202 is mounted, as shown in FIG. 3. The ultrasound probe 302 can provide visuals based on which a physician can guide the first end 202-1 of the needle 202 towards an ovarian follicle. Thus, the ultrasound probe 302 facilitates in locating the ovarian follicle. The ultrasound probe 302 has a gripping handle 304 which can be held by a physician while performing aspiration of the follicular fluid. The system 100 includes a needle guide 306 which is fixed to the ultrasound probe 302 through a clamping. In an example, the needle guide 306 is a metallic or plastic hollow cylinder mounted on the ultrasonic probe 302 allowing passage of the needle 202 through it. The needle guide 306 enables back and forth movement of the needle 202 for piercing the follicle and aspiration of follicular fluid.

In operation, the physician may hold the ultrasound probe 302 in one hand and grip the handle 208 and first elastic tube 210 in the other hand. The handle 208 and the first elastic tube 210 may be held in a single grip between an index finger and a thumb. In an example, the ultrasound probe 302 may be a transvaginal ultrasound probe which is used to locate the ovary of the prospective mother. The ultrasound probe provides visuals of the internal structure of the ovary. The physician by analyzing these visuals can locate an ovarian follicle inside the ovary and guide the first end 202-1 of the needle 202 towards the ovarian follicle. Once the first end 202-1 of the needle 202 is positioned towards the ovarian follicle, the physician moves forward the needle 202 through the needle guide 306 which is held stably at a predefined angle thereby puncturing the wall of the ovarian follicle and the suction pump 104 is turned on. The suction pump 104 operates, thereby creating a suction force acting through the lumen of the needle 202 and aspirates the follicular fluid from the follicle. The follicular fluid gets collected in the collection chamber 102.

Figure 4:
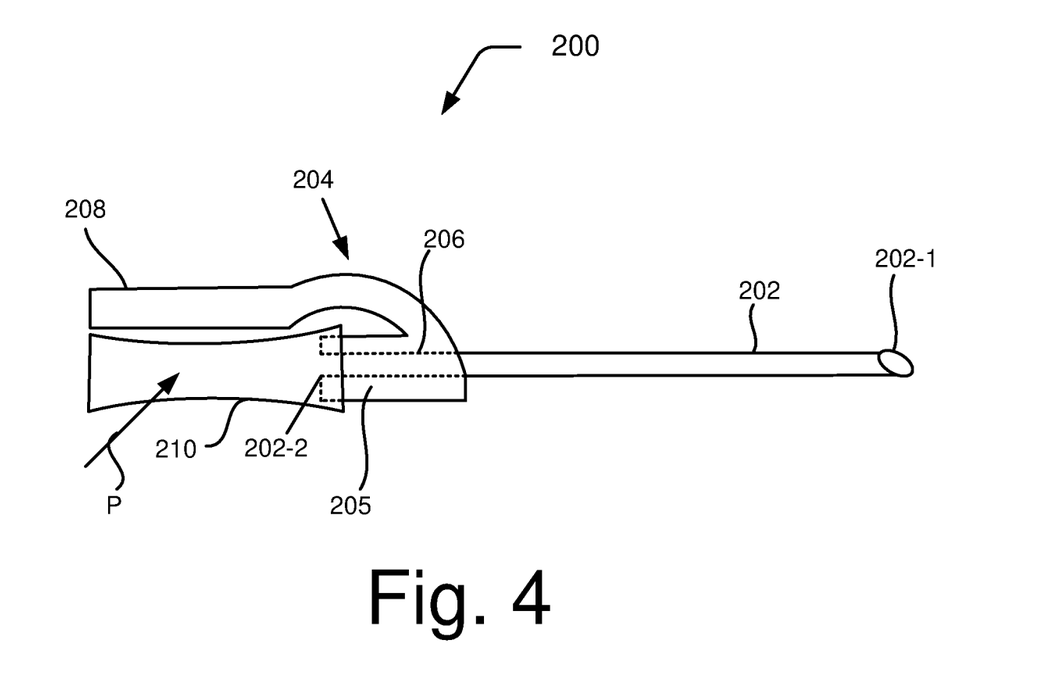
FIG. 4 illustrates an elastic tube of the system in a compressed condition, according to an example.

After the follicular fluid from one follicle is completely aspirated, the physician pinches the first elastic tube 210 thereby compressing the first elastic tube 210, as shown in FIG. 4. The arrow P in FIG. 4 indicates the direction of application of force for pinching the first elastic tube 210. In an example, the first elastic tube 210 may be pinched from two sides between two fingers, such as a thumb and an index or any other finger of the same hand. The handle 208 is positioned with respect to the first elastic tube 210, such that the elastic tube 210 is pinchable by movement of the index finger and the thumb towards each other, while the handle 208 is gripped between the index finger and the thumb. The compression of the first elastic tube 210 reduces the suction force. In an example, compression of the first elastic tube 210 may reduce the suction force to 0 thereby completely eliminating the suction force and stopping the aspiration of any fluid(s) through the needle 202. Thus, the handle 208 provides an ergonomic grip to the physician who can regulate the suction force by pinching the first elastic tube 210 while locating the ovarian follicle and piercing the needle 202 through the ovarian follicle.

The first end 202-1 of the needle 202 is then passed through inter follicular ovarian tissue. Since, the suction force is reduced or eliminated by the pinching of the first elastic tube 210, fluid pressure inside the needle 202 is higher compared to the fluid pressure in the ovary which prevents aspiration of blood and ovarian tissue while the needle 202 moves through the inter follicular ovarian tissue. Thus, blood stains are prevented from getting mixed with the follicular fluid accumulated in the collection chamber 102. Also, trauma to the ovary due to blood loss resulting from undesired aspiration of blood or aspiration of ovarian tissue is minimized or eliminated.

As the physician, guided by the ultrasound probe, moves the needle 202 so that the first end 202-1 of the needle 202 touches another ovarian follicle, the physician punctures the follicular wall by forward movement of the needle 202 and releases the pinch on the first elastic tube 210. As the pinch on the first elastic tube 210 is released, the first elastic tube 210 gets decompressed, as shown in FIG. 2, and the suction force increases. The increased suction force draws out the follicular fluid from the follicle and completely aspirates the follicle while the follicular fluid gets accumulated in the collection chamber 102.

This process of compressing and decompressing the first elastic tube 210 may be carried out as the needle 202 is moved through the ovary from one follicle to another follicle. The follicular fluid collected in the collection chamber 102, in the above manner, contains minimal or no blood stains and thereby the aspirated follicular fluid retains its optimal physiological conditions and thereby may result in a higher rate of fertilization when used for IVF.

Further, as the follicular fluid gets accumulated in the collection chamber 102, the collection chamber may get completely filled. Thus, the collection chamber 102 may be required to be replaced by another collection chamber, similar to the collection chamber 102. When the collection chamber 102 is filled with follicular fluid, to replace the collection chamber, the stopper 103 containing first connecting tube 106 and third connecting tube 112 may be pulled out from the collection chamber 102. When the stopper 103 is pulled out, the suction force provided by the suction pump 104 is absent which may result in generation of a negative pressure inside the ovary. Due to the negative pressure created inside the ovary, the follicular fluid accumulated in the collection chamber 102 may flow back into the ovary.

In order to prevent the backflow, in an example, the second elastic tube 110 may be compressed or pinched against the stopper 103. Compression of the second elastic tube 110 against the stopper 103 may prevent the backflow of the follicular fluid thereby reducing/eliminating loss of the follicular fluid while the collection chamber is replaced. Further, since the second elastic tube 110 is proximal to the collection chamber 102, the second elastic tube 110 may be compressed or pinched by an assistant of the physician performing the aspiration, while the physician is engaged in locating and piercing the follicles for aspiration thereby facilitating an uninterrupted follicular aspiration.

Figure 5A:
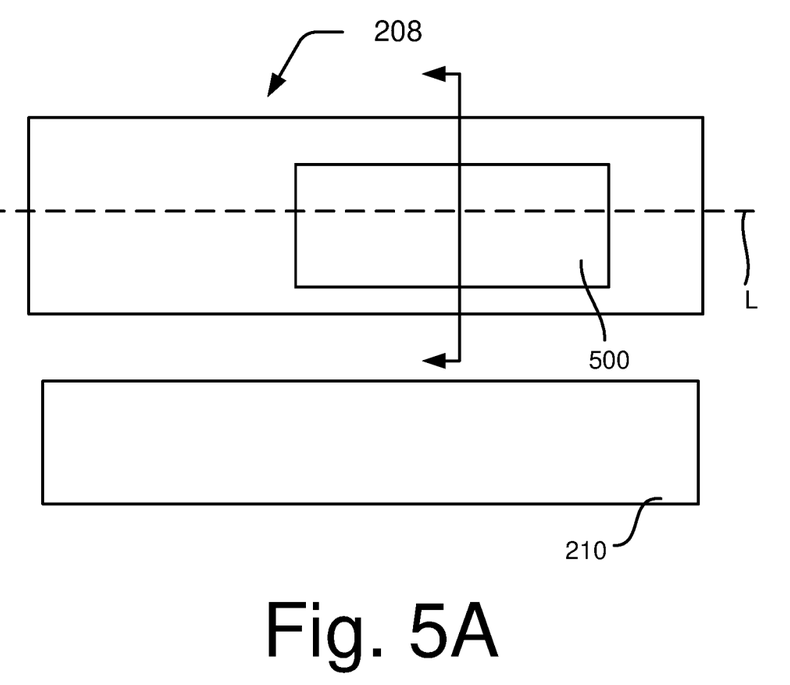
FIG. 5A illustrates a portion of the OPU device with a handle and an elastic tube, according to an example.

FIG. 5A illustrates a portion of the OPU device 200 with the handle 208 and the elastic tube 210, according to an example. The handle 208 has a cylindrical shape and includes a pinch profile 500 formed in a portion of the handle thereof. The pinch profile 500 is formed by a slotted portion of the handle 208. When the handle 208 is held by a physician, the pinch profile 500 may be gripped between the forefinger on one side and the thumb on the other side. The handle 208 has a longitudinal axis L passing along a length of the handle 208. Cross-sectional views of the pinch profile 500 are illustrated through FIGS. 5B to 5D.

Figure 5B:
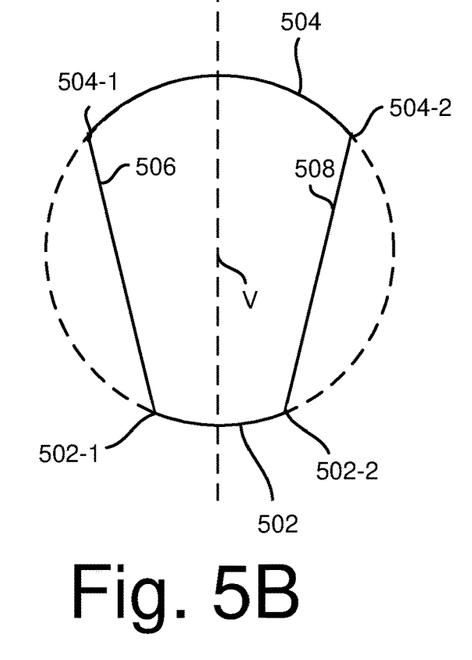
FIGS. 5B to 5D illustrate cross-sectional views of a pinch profile in the handle of the OPU device, according to an example.

As shown in FIG. 5B, the pinch profile has a cross-sectional shape with a first edge 502, a second edge 504 opposite to the first edge 502, a third edge 506, and a fourth edge 508 opposite to the third edge 506. The first edge 502 has a first endpoint 502-1 and a second endpoint 502-2 opposite to the first endpoint 502-1. The second edge 504 has a first endpoint 504-1 and a second endpoint 504-2 opposite to the first endpoint 504-1. The first endpoints 502-1 and 504-1 of the first and second edges 502 and 504, respectively, are positioned on a first side of a vertical plane, represented by line V, in FIGS. 5B to 5D, passing through the longitudinal axis L of the handle 208. The second endpoints 502-2 and 504-2 of the first and second edges 502 and 504, respectively, are positioned on a second side, opposite to the first side, of the vertical plane V. The third edge 506 connects the first endpoint 502-1 of the first edge 502 to a first endpoint 504-1 of the second edge 504. The fourth edge 508, connects the second endpoint 502-2 of the first edge 502 to the second endpoint 504-2 of the second edge 504.

The first edge 502 is proximal to the elastic tube 210 and the second edge 504 is distal to the elastic tube 210. The first edge 502 is of a smaller length than a length of the second edge 504. The length of the first edge 502 is smaller than a cross-sectional diameter of the elastic tube 210. In an example, the length of the first edge 502 is less than or equal to a cross-sectional diameter of the elastic tube 210 when fully compressed.

Figure 5C:
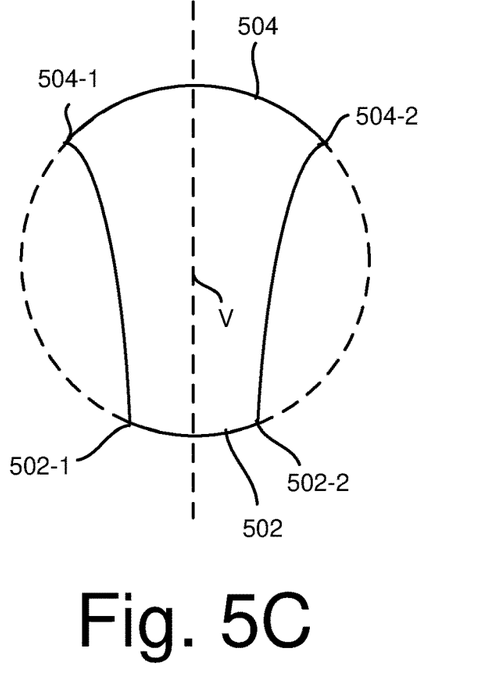
Figure 5D:
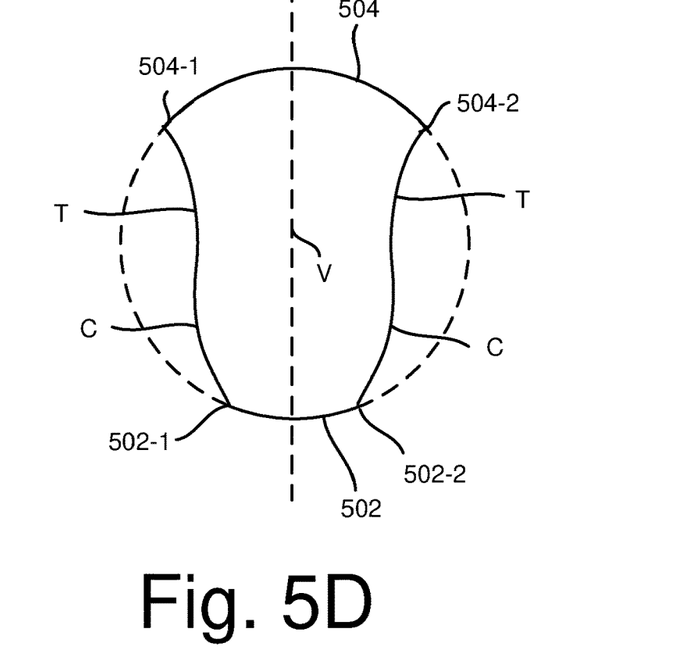

Although in FIG. 5B, the third and fourth edges 506 and 508 are illustrated to have a straight-line profile, the third and fourth edges 506 and 508 may have curved profiles as shown in FIGS. 5C and 5D. In FIG. 5C the third and fourth edges 506 and 508 are shown to have a convex curve profile. The curved profile of each of the third and fourth edges 506 and 508 has one crest C and one trough T, as illustrated in FIG. 5D. The pinch profile as illustrated through FIGS. 5B to 5D facilitates an efficient pinching of the first elastic tube 210 and simultaneous movement of the needle 202 for piercing the follicle.

Figure 6:
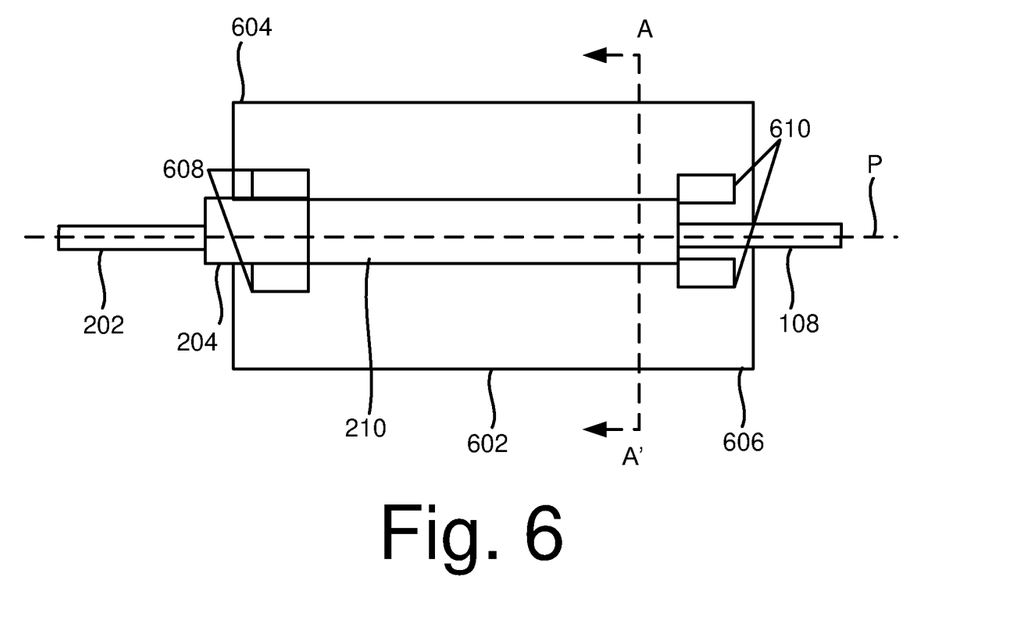
FIG. 6 illustrates a portion of the OPU device with a handle and an elastic tube, according to an example.

FIG. 6 illustrates a handle 602 for the OPU device 100, according to an example. The handle 602 is positioned parallel to the elastic tube 210 and extends along a length of the elastic tube 210. In an example, the handle 602 may be of a cylindrical or tube shape. The handle 602 may be formed of metal, plastic, and the like. The handle 602 has a width greater than a cross-sectional diameter of the elastic tube 210.

The handle 602 is positioned perpendicular to the horizontal plane P passing through the elastic tube 210. The handle 602 has a first end 604 that is proximal to the needle 202. The first end 604 is coupled to the connector 204. Further, the handle 602 has a second end 606 that is opposite to the first end 604. The second end 606 is coupled to the connecting tube 108, which enables the follicular fluid to be transferred from the elastic tube 210 to the collection chamber 102. The handle 602 provides an ergonomic grip to the physician who can regulate the suction force by pinching the elastic tube 210 while locating the ovarian follicle and piercing the needle 202 through the ovarian follicle. In an example, the elastic tube 210 may be pinched by compressing the elastic tube 210 against one side of the handle 602 by one finger, while the handle 602 may be supported by another finger on the other side.

Further, the handle 602 includes a first pair of projections 608 at the first end 604. The first pair of projections 608 may be made up of metal. The first pair of projections 608 are extended portions that are parallel to the horizontal plane P passing through the elastic tube 210. The first pair of projections 608 holds a portion of the connector 204 between them.

The handle 602 includes a second pair of projections 610 that is opposite to the first pair of projections 608, at the second end 606. The second pair of projections 610 may be made up of metal. The second pair of projections 610 are extended portions that are parallel to the horizontal plane P passing through the elastic tube 210. The second pair of projections 610 enables a portion of the connecting tube 108 to be held between them.

Figure 7:
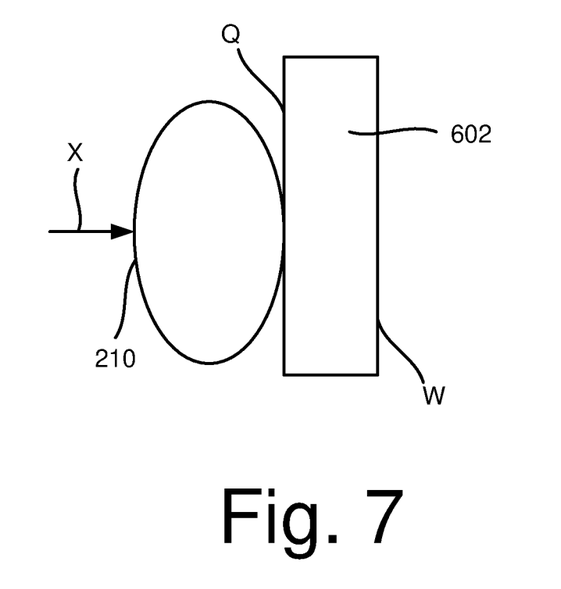
FIG. 7 illustrates a cross-sectional view of the elastic tube pinched against the handle, according to an example.

FIG. 7 illustrates a cross-sectional view of the elastic tube 210 pinched against the handle 602, according to an example. The cross-sectional view of FIG. 7 may be obtained by viewing the OPU device along the line AA' and in the direction of the arrows, as illustrated in FIG. 6. With reference to FIG. 7, the handle 602 has two faces. The handle 602 has a first face Q towards the elastic tube 210 and a second face W opposite to the first face Q.

In an example, a physician operating the OPU device may place his forefinger against the second face W of the handle 602. The physician may then compress the elastic tube 210 along the direction of the arrow X, such that the elastic tube 210 touches and is pressed against the first face Q of the handle 602. The forefinger held against the second face W acts as a support for compressing the elastic tube 210. In this manner, the elastic tube 210 may be compressed conveniently with two fingers.

Figure 8:
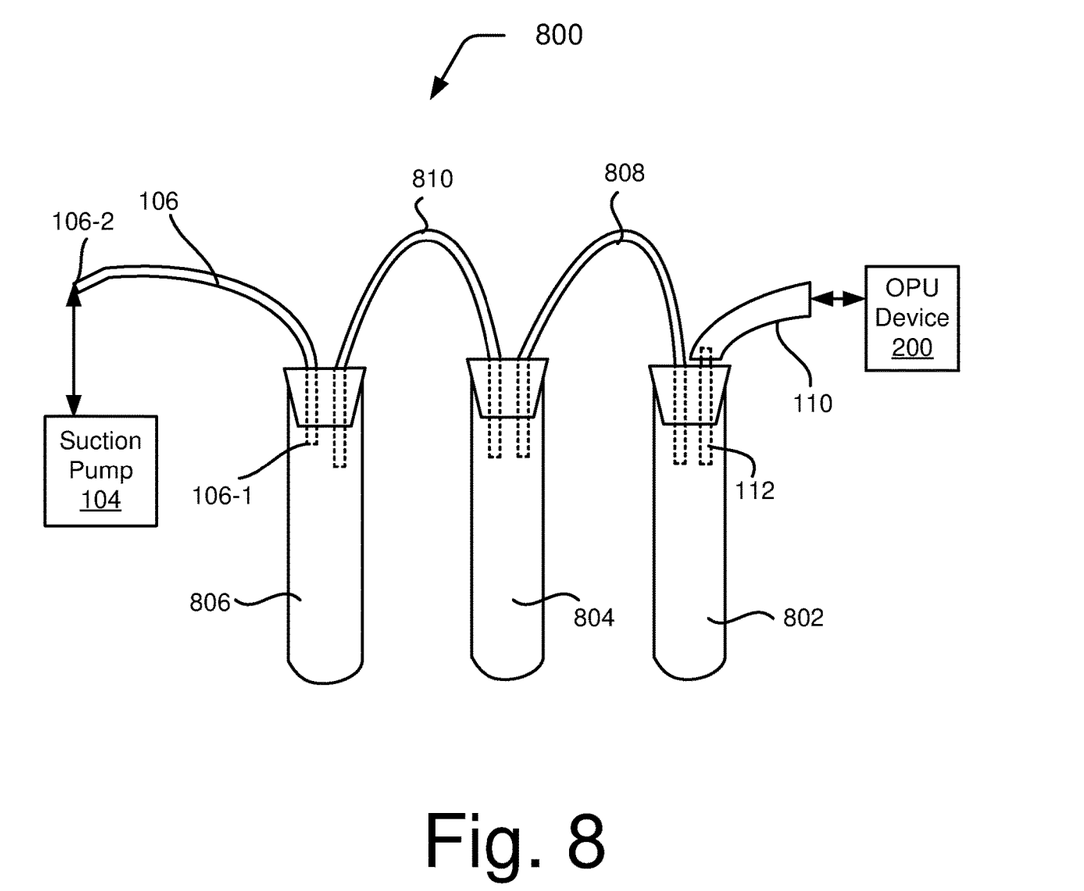
FIG. 8 illustrates a tandem connection of collection chambers in the system for aspirating follicular fluid from ovarian follicles, according to an example.

FIG. 8 illustrates a tandem connection 800 of collection chambers in the system 100 for aspirating follicular fluid from ovarian follicles, according to an example. In an example, the tandem connection of collection chambers refers to a cascade connection of a set of collection chambers connected between an OPU device, such as the OPU device 200, and a suction pump, such as the suction pump 104.

As shown in FIG. 8, the tandem connection includes a first collection chamber 802, a second collection chamber 804, and a third connection chamber 806. Although three collection chambers are shown in the tandem connection 800, there may be more than three collection chambers in the tandem connection. In the tandem connection 800, the first collection chamber 802 is proximal to the OPU device 200, and the third collection chamber 806 is proximal to the suction pump 104. The first collection chamber 802 is connected to the second connection chamber 804 through a first cascade connector 808. The second collection chamber 804 is connected to the third connection chamber 806 through a second cascade connector 810. The first and second cascade connectors may be connecting tubes or pipes, such as the connecting tube 106. In an example, each of the first, second, and third collection chambers 802, 804, and 806 may have a volume of 14 ml.

With reference to FIG. 8, the third connecting tube 112 carries the follicular fluid from the second elastic tube 110 to the first collection chamber 802. The first end 106-1 of the first connecting tube 106 resides inside the third collection chamber 606 and a second end 106-2 is coupled to the suction pump 104 through coupling elements (not shown).

Follicular fluid in a range of about 2 ml to about 70 ml may be collected from a single ovary. With a single connection chamber in the system, the collection chamber is to be replaced multiple times to enable complete aspiration of the single ovary. With the tandem connection 800 of collection chambers, follicular fluid in a range of about 10 ml to about 150 ml may be collected without changing the collection chambers which facilitates uninterrupted follicular aspiration by the physician.

Although implementations of present subject matter have been described in language specific to structural features and/or methods, it is to be noted that the present subject matter is not necessarily limited to the specific features or methods described. Rather, the specific features and methods are disclosed and explained in the context of a few implementations for the present subject matter.

We claim:

1. An ovum pick up device for aspirating follicular fluid from ovarian follicles, the ovum pick up device comprising:
   a needle having a first end and a second end, opposite to the first end, wherein the first end of the needle is to pierce through an ovarian follicle to aspirate the follicular fluid from the ovarian follicle by a suction force;
   a connector having a channel to receive the second end of the needle; and
   an elastic tube connected to the connector, wherein the second end of the needle passes through the channel and inside the elastic tube, wherein the elastic tube is compressible, while locating the ovarian follicle and piercing the needle through the ovarian follicle, to regulate the suction force during aspiration of the follicular fluid, wherein the connector comprises:
      a main body, wherein the channel is a through hole formed in the main body; and
      a handle protruding out from the main body, wherein the handle extends parallel to the elastic tube and along a length of the elastic tube.

2. The ovum pick up device as claimed in claim 1, wherein the handle has a cylindrical shape and a pinch profile in a portion thereof, wherein the pinch profile has a cross-sectional shape with:
   a first edge proximal to the elastic tube; and
   a second edge opposite to the first edge and distal to the elastic tube, the first edge being of a smaller length than a length of the second edge and a cross-sectional diameter of the elastic tube.

3. The ovum pick up device as claimed in claim 2, wherein the cross-sectional shape is further with:
   a third edge connecting a first endpoint of the first edge to a first endpoint of the second edge, the first endpoint of the first edge and the first end point of the second edge being positioned on a first side of a vertical plane passing through a longitudinal axis of the handle; and
   a fourth edge, opposite to the third edge, connecting a second endpoint of the first edge to a second endpoint of the second edge, the second endpoint of the first edge and the second end point of the second edge being positioned on a second side, opposite to the first side, of the vertical plane.

4. The ovum pick up device as claimed in claim 3, wherein each of the third edge and the fourth edge has a straight-line profile.

5. The ovum pick up device as claimed in claim 3, wherein each of the third edge and the fourth edge has a curved profile.

6. The ovum pick up device as claimed in claim 5, wherein the curved profile has one crest and one trough.

7. The ovum pick up device as claimed in claim 1, wherein the elastic tube is compressible when pinched between an index finger and a thumb.

8. The ovum pick up device as claimed in claim 1, wherein the handle is perpendicular to a horizontal plane passing through the elastic tube, and wherein the handle has a first end proximal to the needle, the first end being coupled to the connector, and a second end opposite to the first end, the second end being coupled to a connecting tube that is to carry the follicular fluid from the elastic tube to a collection chamber.

9. The ovum pick up device as claimed in claim 8, wherein the handle has a first pair of projections at the first end, such that a portion of the connector is held between the first pair of projections.

10. The ovum pick up device as claimed in claim 8, wherein the handle has a second pair of projections at the second end, such that a portion of the connecting tube is held between the second pair of projections.

11. The ovum pick up device as claimed in claim 8, wherein the handle has a width greater than a cross-sectional diameter of the elastic tube.

12. The ovum pick up device as claimed in claim 1, wherein the elastic tube has a length ranging from about 1 cm to about 10 cm.

13. The ovum pick up device as claimed in claim 1, wherein the elastic tube has an inner diameter one of equal to or greater than an outer diameter of the needle.

14. The ovum pick up device as claimed in claim 1, wherein the elastic tube is made of one of rubber or silicon.

15. A system for aspirating a follicular fluid from ovarian follicles, the system comprising:
- a collection chamber for accumulation of the follicular fluid;
- a suction pump coupled to the collection chamber, wherein the suction pump is to generate a suction force to aspirate the follicular fluid from an ovarian follicle;
- a needle having a first end and a second end, opposite to the first end, wherein the first end of the needle is to pierce through the ovarian follicle to draw the follicular fluid from the ovarian follicle by the suction force;
- a connector having a channel to receive the second end of the needle; and
- a first elastic tube connected to the connector, wherein the second end of the needle passes through the channel and inside the first elastic tube, wherein the first elastic tube is compressible, while locating the ovarian follicle and piercing the needle through the ovarian follicle simultaneously, to regulate the suction force during aspiration of the follicular fluid, wherein the connector comprises:
- a main body, wherein the channel is a through hole formed in the main body; and
- a handle integral to the main body, wherein the handle is parallel to the first elastic tube and extends along a length of the first elastic tube.

16. The system as claimed in claim 15, further comprising:
- a set of collection chambers connected between the suction pump and the collection chamber, wherein collection chambers in the set are connected through a cascade connection of connector pipes.

17. The system as claimed in claim 15, further comprising:
- a connecting tube having a first end coupled to an end of the first elastic tube and a second end facing towards the collection chamber, wherein the connecting tube is to carry the follicular fluid from the first elastic tube to the collection chamber.

18. The system as claimed in claim 17, further comprising:
- a second elastic tube connected between the connecting tube and the collection chamber, wherein an end of the second elastic tube is proximal to the collection chamber and the second elastic tube is compressible to control backflow of follicular fluid into an ovary while the collection chamber is replaced.

19. The system as claimed in claim 18, wherein a length of the second elastic tube ranges between about 1 cm to about 2 cm.

20. The system as claimed in claim 15, further comprising:
- an ultrasound probe on which a needle guide is mounted through which the needle is passed, wherein the ultrasound probe is to guide the first end of the needle towards the ovarian follicle.

* * * * *